US010231946B2

(12) United States Patent
Hughes et al.

(10) Patent No.: US 10,231,946 B2
(45) Date of Patent: Mar. 19, 2019

(54) METHODS OF TREATING ISCHEMIC ORGAN DAMAGE AND OTHER DISORDERS

(71) Applicant: Zafgen, Inc., Boston, MA (US)

(72) Inventors: Thomas E. Hughes, Boston, MA (US); James E. Vath, Lynnfield, MA (US)

(73) Assignee: Zafgen, Inc., Boston, MA (US)

( * ) Notice: Subject to any disclaimer, the term of this patent is extended or adjusted under 35 U.S.C. 154(b) by 0 days.

(21) Appl. No.: 15/813,726

(22) Filed: Nov. 15, 2017

(65) Prior Publication Data

US 2018/0085338 A1    Mar. 29, 2018

Related U.S. Application Data

(63) Continuation of application No. 15/423,863, filed on Feb. 3, 2017, now Pat. No. 9,849,106, which is a continuation of application No. 14/776,103, filed as application No. PCT/US2014/028022 on Mar. 14, 2014, now Pat. No. 9,597,309.

(60) Provisional application No. 61/787,769, filed on Mar. 15, 2013, provisional application No. 61/781,926, filed on Mar. 14, 2013.

(51) Int. Cl.
*A61K 31/335* (2006.01)
*A61K 31/336* (2006.01)
*A61K 31/713* (2006.01)
*A61P 13/12* (2006.01)

(52) U.S. Cl.
CPC .......... *A61K 31/336* (2013.01); *A61K 31/335* (2013.01); *A61K 31/713* (2013.01); *A61P 13/12* (2018.01)

(58) Field of Classification Search
CPC .................................................... A61K 31/335
USPC ........................................................ 514/475
See application file for complete search history.

(56) References Cited

U.S. PATENT DOCUMENTS

| | | | |
|---|---|---|---|
| 5,164,410 A | 11/1992 | Kishimoto et al. | |
| 5,166,172 A | 11/1992 | Kishimoto et al. | |
| 5,180,735 A | 1/1993 | Kishimoto et al. | |
| 5,180,738 A | 1/1993 | Kishimoto et al. | |
| 5,196,406 A | 3/1993 | Kamei et al. | |
| 5,204,345 A | 4/1993 | Kishimoto et al. | |
| 5,288,722 A | 2/1994 | Kishimoto et al. | |
| 5,290,807 A | 3/1994 | Folkman et al. | |
| 5,422,363 A | 6/1995 | Yanai et al. | |
| 5,536,623 A | 7/1996 | Ohmachi et al. | |
| 5,698,586 A | 12/1997 | Kishimoto et al. | |
| 5,767,293 A | 6/1998 | Oku et al. | |
| 5,846,562 A | 12/1998 | Yanai et al. | |
| 5,900,431 A | 5/1999 | Molina et al. | |
| 6,017,949 A | 1/2000 | D'Amato et al. | |
| 6,017,954 A | 1/2000 | Folkman et al. | |
| 6,040,337 A | 3/2000 | Hong, II et al. | |
| 6,063,812 A | 5/2000 | Hong et al. | |
| 6,180,626 B1 | 1/2001 | Shimomura et al. | |
| 6,207,704 B1 | 3/2001 | Liu et al. | |
| 6,242,494 B1 | 6/2001 | Craig et al. | |
| 6,277,391 B1 | 8/2001 | Seo et al. | |
| 6,306,819 B1 | 10/2001 | Rupnick et al. | |
| 6,323,228 B1 | 11/2001 | BaMaung et al. | |
| 6,383,471 B1 | 5/2002 | Chen et al. | |
| 6,548,477 B1 | 4/2003 | Olson et al. | |
| 6,566,541 B2 | 5/2003 | Liu et al. | |
| 6,664,244 B1 | 12/2003 | Furuse et al. | |
| 6,803,382 B2 | 10/2004 | Eustache et al. | |
| 6,877,863 B2 | 4/2005 | Wood et al. | |
| 6,989,392 B2 | 1/2006 | Collins et al. | |
| 7,030,262 B2 | 4/2006 | BaMaung et al. | |
| 7,037,890 B2 | 5/2006 | Olson et al. | |
| 7,084,108 B2 | 8/2006 | Olson et al. | |
| 7,268,111 B2 | 9/2007 | Olson et al. | |
| 7,304,082 B2 | 12/2007 | Marino, Jr. et al. | |
| 7,718,695 B2 | 5/2010 | Kim et al. | |
| 8,367,721 B2 | 2/2013 | Hughes et al. | |
| 8,642,650 B2 | 2/2014 | Hughes et al. | |
| 8,980,946 B2 | 3/2015 | Hughes | |
| 9,000,035 B2 | 4/2015 | Hughes | |
| 9,173,865 B2 | 11/2015 | Hughes | |
| 9,446,016 B2 | 9/2016 | Hughes et al. | |
| 9,597,309 B2 | 3/2017 | Hughes et al. | |
| 9,649,293 B2 | 5/2017 | Hughes et al. | |
| 9,839,622 B2 | 12/2017 | Vath et al. | |
| 2003/0220371 A1 | 11/2003 | Kallander et al. | |
| 2004/0067266 A1 | 4/2004 | Toppo | |
| 2004/0116495 A1 | 6/2004 | Marino, Jr. et al. | |
| 2004/0157836 A1 | 8/2004 | Comess et al. | |
| 2004/0167128 A1 | 8/2004 | Comess et al. | |
| 2004/0204472 A1 | 10/2004 | Briggs et al. | |
| 2005/0037994 A1 | 2/2005 | Kim et al. | |

(Continued)

FOREIGN PATENT DOCUMENTS

EP        0682020 A1    11/1995
WO    WO-1998/056372 A1    12/1998

(Continued)

OTHER PUBLICATIONS

Anderson, "The Use of Fumagillin in Amoebiasis," Annals of the New York Academy of Sciences, 55:1118-1124, 1952.
Benny et al., "An Orally Delivered Small-Molecule Formulation with Antiangiogenic and Anticancer Activity," Nat Biotechnol. Jul. 2008;26(7):799-807.
Bernier et al.,"Fumagillin class inhibitors of methionine aminopeptidase-2," Drugs of the Future 30(5):497-500, 2005.
Brakenhielm et al., "Angiogenesis Inhibitor, TNP-470, Prevents Diet-Induced and Genetic Obesity in Mice" Circulation Research, http://circres.ahajournals.org (accessed on Feb. 8, 2007), 2004.

(Continued)

Primary Examiner — Raymond J Henley, III
(74) Attorney, Agent, or Firm — Goodwin Procter LLP

(57) ABSTRACT

The invention generally relates to methods of treating a patient suffering from renal disorders or other disorders related to low levels of sRAGE, and/or low levels of adiponectin (e.g., high molecular weight adiponectin) and/or high levels of thrombomodulin, using effective of amounts of a MetAP-2 inhibitor.

10 Claims, 5 Drawing Sheets

(56) References Cited

U.S. PATENT DOCUMENTS

| | | |
|---|---|---|
| 2005/0239878 A1 | 10/2005 | Thompson et al. |
| 2006/0045865 A1 | 3/2006 | Jacob et al. |
| 2006/0069161 A1 | 3/2006 | Lee et al. |
| 2006/0276512 A1 | 12/2006 | Han et al. |
| 2007/0078172 A1 | 4/2007 | McElroy et al. |
| 2008/0200402 A1 | 8/2008 | Alvinerie et al. |
| 2009/0148396 A1 | 6/2009 | Akullian et al. |
| 2010/0016425 A1 | 1/2010 | Vath |
| 2010/0111894 A1 | 5/2010 | Benny-Ratsaby et al. |
| 2012/0004162 A1 | 1/2012 | Vath |
| 2012/0010259 A1 | 1/2012 | Vath |
| 2012/0010290 A1 | 1/2012 | Vath |
| 2012/0034233 A1 | 2/2012 | Hughes et al. |
| 2012/0322867 A1 | 12/2012 | Hughes et al. |
| 2013/0052283 A1 | 2/2013 | Vath |
| 2013/0316994 A1 | 11/2013 | Hughes |
| 2014/0011870 A1 | 1/2014 | Hughes |
| 2014/0045934 A1 | 2/2014 | Hughes |
| 2014/0045935 A1 | 2/2014 | Hughes |
| 2014/0051752 A1 | 2/2014 | Hughes |
| 2014/0336251 A1 | 11/2014 | Hughes et al. |
| 2015/0180840 A1 | 6/2015 | Jung et al. |
| 2015/0209320 A1 | 7/2015 | Hughes et al. |
| 2015/0209321 A1 | 7/2015 | Hughes |
| 2015/0335608 A1 | 11/2015 | Hughes et al. |
| 2016/0243073 A1 | 8/2016 | Hughes |
| 2017/0196829 A1 | 7/2017 | Hughes et al. |
| 2017/0333383 A1 | 11/2017 | Hughes et al. |

FOREIGN PATENT DOCUMENTS

| | | |
|---|---|---|
| WO | WO-1999/039702 A2 | 8/1999 |
| WO | WO-1999/057097 A2 | 11/1999 |
| WO | WO-1999/059986 A1 | 11/1999 |
| WO | WO-1999/059987 A1 | 11/1999 |
| WO | WO-2000/064876 A1 | 11/2000 |
| WO | WO-2002/026782 A2 | 4/2002 |
| WO | WO-2002/042295 A2 | 5/2002 |
| WO | WO-2002/083065 A2 | 10/2002 |
| WO | WO-2003/027104 A1 | 4/2003 |
| WO | WO-2003/082845 A1 | 10/2003 |
| WO | WO-2004/033419 A1 | 4/2004 |
| WO | WO-2005/066197 A2 | 7/2005 |
| WO | WO-2005/082349 A1 | 9/2005 |
| WO | WO-2006/010498 A2 | 2/2006 |
| WO | WO-2006/080591 A1 | 8/2006 |
| WO | WO-2009/036108 A1 | 3/2009 |
| WO | WO-2009/073445 A2 | 6/2009 |
| WO | WO-2010/042163 A2 | 4/2010 |
| WO | WO-2010/048499 A1 | 4/2010 |
| WO | WO-2010/065877 A2 | 6/2010 |
| WO | WO-2010/065879 A2 | 6/2010 |
| WO | WO-2010/065881 A2 | 6/2010 |
| WO | WO-2010/065883 A2 | 6/2010 |
| WO | WO-2011/044506 A2 | 4/2011 |
| WO | WO-2011/085198 A1 | 7/2011 |
| WO | WO-2011/085201 A1 | 7/2011 |
| WO | WO-2011/088055 A2 | 7/2011 |
| WO | WO-2011/127304 A2 | 10/2011 |
| WO | WO-2011/150338 A1 | 12/2011 |
| WO | WO-2012/012642 A1 | 1/2012 |
| WO | WO-2012/064838 A1 | 3/2012 |
| WO | WO-2012/051318 A1 | 4/2012 |
| WO | WO-2012/064928 A1 | 5/2012 |
| WO | WO-2012/074968 A1 | 6/2012 |
| WO | WO-2012/075020 A1 | 6/2012 |
| WO | WO-2012/075026 A1 | 6/2012 |
| WO | WO-2012/103333 A1 | 8/2012 |
| WO | WO-2012/122264 A1 | 9/2012 |
| WO | WO-2012/154676 A1 | 11/2012 |
| WO | WO-2012/154678 A1 | 11/2012 |
| WO | WO-2012/154679 A1 | 11/2012 |
| WO | WO-2013/033430 A1 | 3/2013 |
| WO | WO-2013/055385 A2 | 4/2013 |
| WO | WO-2013/109735 A1 | 7/2013 |
| WO | WO-2013/109739 A1 | 7/2013 |
| WO | WO-2013/169727 A1 | 11/2013 |
| WO | WO-2013/169860 A1 | 11/2013 |

OTHER PUBLICATIONS

Braunwald et al., "Obesity" in Harrison's Principles of Internal Medicine, 15th Ed., McGraw Hill (New York) pp. 479-486, 2001.

Butler et al., "Clinical Findings and Natural History of Prader-Willi Syndrome," Chapter 1; Clinical Findings and Natural History of PWS, pp. 3-48 (2006).

Cassidy et al., "Prader-Willi syndrome," European Journal of Human Genetics 17:3-13 (2009).

Cassidy et al., "Prader-Willi syndrome," Genetics in Medicine, vol. 14(1) pp. 10-26 (2012).

Cataletto et al., "Prader-Willi syndrome: A primer for clinicians," International Journal of Pediatric Endocrinology, vol. 12:1-13 (2011).

Chun et al., "Novel inhibitors targeted to methionine aminopeptidase 2 (MetAP2) strongly inhibit the growth of cancers in xenografted nude model," Int J Cancer. Mar. 10, 2005;114(1):124-30.

Didier et al., "Antimicrosporidial Activities of Fumagillin, TNP-470, Ovalicin, and Ovalicin Derivatives in Vitro and In Vivo" Antimicrob Agents Chemother. Jun. 2006;50(6):2146-55.

DiPaolo et al., "Studies on the Carcinolytic Activity of Fumagillin and Some of its Derivatives," Antibiot Annu.1958-1959;6:541-6.

Drevs et al.,"Antiangiogenic Potency of FK866/K22.175, a New Inhibitor of Intracellular NAD Biosynthesis, in Murine Renal Cell Carcinoma," Anticancer Res. Nov.-Dec. 2003;23(6C):4853-4858.

Dumas et al., "Synthesis and Structure Activity Relationships of Novel Small Molecule Cathepsin D Inhibitors" Bioorg Med Chem Lett. Sep. 6, 1999;9(17):2531-6.

Dykens et al., "Assessment of Hyperphagia in Prader-Willi Syndrome," Obesity 15:7 (2007).

Eder et al., "Phase 1 Dose Escalation Safety & Tolerance Study of PPI-2458 in Subjects with Non-Hodgkin's Lymphoma or Solid Tumors" (Presented on Nov. 7-10, 2006 at EORTC-NCI-AACR Symposium on "Molecular Targets and Cancer Therapeutics.").

Edgar et al., "Body composition in Prader-Willi syndrome compared with nonsyndromal obesity: Relationship to physical activity and growth homrone function," The Journal of Pediatrics 139:5, 708-714 (2001).

Einfield et al., "Mortality in Prader-Willi Syndrome," Am. J. Ment. Retard. 111(3):193-198 (2006).

European Communication for EP Application No. 12 798 444.1, dated Aug. 28, 2015 (8 pages).

European Search Report for EP 09798793 dated Oct. 11, 2011, 9 pages.

Evdokimov et al., "Serendipitious discovery of novel bacterial methionine aminopeptidase inhibitors," Proteins Feb. 15; 66(3):538-546 (2007).

Everhart, "Contributions of Obesity and Weight Loss to Gallstone Disease" Ann Intern Med. Nov. 15, 1993;119(10):1029-35.

Garrabrant et al.,"Small molecule inhibitors of methionine aminopeptidase type 2 (MetAP-2) fail to inhibit endothelial cell proliferation or formation of microvessels from rat aortic rings in vitro" Angiogenesis. 2004;7(2):91-6.

Garrison et al., "A metabolic basis for fibromyalgia and its related disorders: the possible role of resistance to thyroid hormone," Med. Hypotheses. Aug.;61(2):182-189 (2003).

Han et al., "Design and Synthesis of Highly Potent Fumagillin Analogues from Homology Modeling for a Human MetAP-2," Bioorg Med Chem Lett. Jan. 3, 2000;10(1):39-43.

Holland et al., "The paradoc of Prader-Willi syndrome: a genetic model of starvation," The Lancet 362, 989-991 (2003).

Huang et al., "Inhibition of Monometalated Methionine Aminopeptidase: Inhibitor Discovery and Crystallographic Analysis," J. Med. Chem., Nov. 15;50(23):5735-5742 (2007).

Ingber et al., "Synthetic Analogues of Fumagillin that Inhibit Angiogenesis and Suppress Tumour Growth," Nature, 348(6301):555-557 (1990).

International Search Report for International Application No. PCT/US2010/052050, dated Mar. 25, 2011, 3 pages.

(56) References Cited

OTHER PUBLICATIONS

International Search Report for International Application No. PCT/US2011/020515, dated May 4, 2011, 4 pages.
International Search Report for International Application No. PCT/US2011/020866, dated Jul. 22, 2011, 8 pages.
International Search Report for International Application No. PCT/US2011/060127, dated Jan. 2, 2012, 2 pages.
International Search Report for International Application No. PCT/US2011/062320, dated Feb. 17, 2012, 3 pages.
International Search Report for International Application No. PCT/US2011/062421, dated Feb. 17, 2012, 3 pages.
International Search Report for International Application No. PCT/US2011/38352, dated Oct. 31, 2011 3 pages.
International Search Report for International Application No. PCT/US2012/000461, dated May 2, 2013, 7 pages.
International Search Report for International Application No. PCT/US2014/028022, dated Oct. 9, 2014, 7 pages.
Jauregi et al., "Behavioral profile of adults with Prader-Willi syndrome: correlations with individual and environmental variables," Journal of Neurodevelopmental Disorders 5:18, 1-10 (2013).
Jeong et al, "Total synthesis and antiangiogenic activity of cyclopentane analogues of fumagillol" Bioorg Med Chem Lett. Aug. 1, 2005;15(15):3580-3.
Kawai et al., "Development of Sulfonamide Compounds as Potent Methionine Aminopeptidase Type II Inhibitors with Antiproliferative Properties", Bioorg. Med. Chem. Lett. Jul. 1;16(13):3574-3577 (2006).
Kim et al. "Assessment of the Anti-Obesity Effects of the TNP-470 Analog, CKD-732" J Mol Endocrinol. Apr. 2007;38(4):455-65.
Kim et al. "Development of parenteral formulation for a novel angiogenesis inhibitor, CKD-732 through complexation with hydroxypropyl-beta-cyclodextrin" Int J Pharm. Mar. 19, 2004;272(1-2):79-89.
Kim et al. "General pharmacology of CKD-732, a new anticancer agent: effects on central nervous, cardiovascular, and respiratory system" Biol Pharm Bull. Feb. 2005;28(2):217-23.
Kim et al., "Depletion of Methionine Aminopeptidase 2 does not Alter Cell Response to Fumagillin or Bengamides," Cancer Res., May 1;64(9):2984-2987 (2004).
Kruger, "TNP-470: An Angiogenesis Inhibitor in Clinical Development for Cancer" Expert Opin Investig Drugs. Jun. 2000;9(6):1383-96.
Lee et al. "Absorption, distribution, metabolism, and excretion of CKD-732, a novel antiangiogenic fumagillin derivative, in rats, mice, and dogs" Arch Pharm Res. Feb. 2004;27(2):265-72.
Lee et al. "Design, Synthesis, and Antiangiogenic Effects of a Series of Potent Novel Fumagillin Analogues" Chem Pharm Bull (Tokyo). Jul. 2007;55(7):1024-9.
Lee et al. "Selective N-demethylation of tertiary aminofumagillols with selenium dioxide via a non-classical Polonovski type reaction" Heterocycles 68(5):915-932, 2006.
Lijnen et al. "Fumagillin Reduces Adipose Tissue Formation in Murine Models of Nutritionally Induced Obesity" Obesity (Silver Spring). Dec. 2010;18(12):2241-6. doi: 10.1038/oby.2009.503. Epub Jan. 21, 2010.
Luo et al., "Discovery and Structural Modification of Inhibitors of Methionine Aminopeptidases from *Escherichia coli* and *Saccharomyces cerevisiae*," J. Med. Chem. Jun. 19;46(13):2631-2640 (2003).
Ma et al., "Structural Analysis of Inhibition of *E. coli* Methionine Aminopeptidase: Implication of Loop Adaptability in Selective Inhibition of Bacterial Enzymes," BMC Struct Biol., Dec. 19;7:84 (2007).
Masiero et al. "New Anti-angiogenesis Agents: Review of the Clinical Experience with Carboxyamido-Triazole (CAI), Thalidomide, TNP-470 and Interleukin-12" Angiogenesis. 1997;1(1):23-35.
McCowen et al., "Fumagillin (H-3), a New Antibiotic with Amebicidal Properties" Science. Feb. 23, 1951;113(2930):202-3.

Milkowski et al., "TNP-470" Antiangiogenic Agents in Cancer Therapy, Chapter 22 pp. 385-398, 1999.
Miller et al., "Nutritional Phases in Prader-Willi Syndrome," Am. J. Med. Genet. A. 155A(5): 1040-1049 (2011).
Molina et al. "Potential Efficacy of Fumagillin in Intestinal Microsporidiosis Due to Enterocytozoon Bieneusi in Patients with HIV Infection: Results of a Drug Screening Study" AIDS. Nov. 1997;11(13):1603-10.
Molina et al. "Fumagillin Treatment of Intestinal Microsporidiosis" N Engl J Med. Jun. 20, 2002;346(25):1963-9.
Molina, et al. "Trial of Oral Fumagillin for the Treatment of Intestinal Microsporidiosis in Patients with HIV Infection" AIDS. Jul. 7, 2000;14(10):1341-8.
Mosteller, R.D., "Simplified Calculation of Body-surface Area," N. Engl .J. Med., 317(17):1098 (Oct. 22, 1987).
Myung et al. "The identification of in vitro metabolites of CKD-732 by liquid chromatography/tandem mass spectrometry" Rapid Commun Mass Spectrom. 2002;16(21):2048-53.
Naganuma et al. "Metronomic doxifluridine chemotherapy combined with the anti-angiogenic agent TNP-470 inhibits the growth of human uterine carcinosarcoma xenografts" Cancer Sci. Aug. 2011;102(8):1545-52. doi: 10.1111/j.1349-7006.2011.01998.x. Epub Jul. 3, 2011.
National Task Force on the Prevention and Treatment of Obesity "Very low-calorie diets. National Task Force on the Prevention and Treatment of Obesity, National Institutes of Health" JAMA Aug. 25, 1993;270(8):967-74.
Noel et al. "Increased Risk of Acute Pancreatitis and Biliary Disease Observed in Patients with Type 2 Diabetes" Diabetes Care. May 2009;32(5):834-8. doi: 10.2337/dc08-1755. Epub Feb. 10, 2009.
Pagliarulo et al.,"Gallstone disease and related risk factors in a large cohort of diabetic patients" Dig. Liver Dis., Feb.;36(2):130-134 (2004).
Picoul et al., "Progress in fumagillin synthesis," Pure Appl. Chem. 75(2-3): 235-249 (2003).
Rhee et al., "Angiogenesis inhibitor attenuates parathyroid hormone-induced anabolic effect" Biomed Pharmacother. Jan.;63(1):63-68 (2009).
Rupnick et al., "Adipose Tissue Mass Can be Regulated Through the Vasculature," Proc. Natl. Acad. Sci. U.S.A. Aug. 6;99(16):10730-10735 (2002).
Seneca et al., "Amebiasis: a review. II. Laboratory diagnosis, differential diagnosis and therapy," Am. J. Dig. Dis. Jul.;1(7):310-322 (1956).
Sheppard et al., "3-Amino-2-Hydroxyamides and Related Compounds as Inhibitors of Methionine Aminopeptidase-2", Bioorg. Med. Chem Lett., Feb. 23;14(4):865-868 (2004).
Shin et al., "A Phase I Pharmacokinetic and Pharmacodynamic Study of CKD-732, an Antiangiogenic Agent, in Patients with Refractory Solid Cancer," Invest New Drugs Oct.;28(5):650-658 (2010).
Shin et al., "A Phase 1b pharmacokinetic study of the anti-angiogenic agent CKD-732 used in combination with capecitabine and oxaliplatin (XELOX) in metastatic colorectal cancer patients who progressed on irinotecan-based chemotherapy," Invest. New Drugs, Apr.;30(2):672-680 (2012).
Srikumar et al., "Structural insights on Brugia malayi transglutaminase with cinnamoyl derivatives—a molecular docking approach," International Journal of Pharma and Bio Sciences 3(3):998-1006 (2012).
Towbin et al., "Proteomics-based target identification: bengamides as a new class of methionine aminopeptidase inhibitors," J. Biol. Chem. 278(52):52964-52971 (2003).
Vedantham et al., "Studies towards the synthesis of methionine aminopeptidase inhibitors: diversification utilizing a ROMP-derived coupling reagent", J Comb Chem. Mar.-Apr.;10(2):195-203 (2008).
Wang et al. "Lead optimization of methionine aminopeptidase-2 (MetAP2) inhibitors containing sulfonamides of 5,6-disubstituted anthranilic acids", Bioorg Med Chem Lett. May 15, 2007;17(10):2817-22. Epub Feb. 25, 2007.
Wang et al. "Tumor Suppression by a Rationally Designed Reversible Inhibitor of Methionine Aminopeptidase-2", Cancer Res. 63:7861-7869, 2003.

(56) References Cited

OTHER PUBLICATIONS

Wang et al., "Discovery of inhibitors of *Escherichia coli* methionine aminopeptidase with the Fe(II)-form selectivity and antibacterial activity", J Med Chem. Oct. 9, 2008;51(19):6110-20.

Weinsier et al., "Gallstone Formation and Weight Loss" Obes Res. Jan.;1(1):51-56 (1993).

Weinsier et al., "Medically Safe Rate of Weight Loss for the Treatment of Obesity: A Guideline Based on Risk of Gallstone Formation" Am. J. Med. Feb.;98(2):115-117 (1995).

Winter et al., "Endothelial anb3 Integrin-Targeted Fumagillin Nanoparticles Inhibit Angiogenesis in Atherosclerosis," Arterioscler Thromb Vasc. Biol., Sep.;26(9):2103-2109 (2006).

Written Opinion for International Application No. PCT/US2009/066816, dated Apr. 8, 2010, 3 pages.

Written Opinion for International Application No. PCT/US2011/060127, dated May 10, 2013, 4 pages.

Written Opinion for International Application No. PCT/US2011/062320, dated May 29, 2013, 5 pages.

Yanai et al., "Antitumor Activity of a Medium-chain Triglyceride Solution of the Angiogenesis Inhibitor TNP-470 (AGM-1470) when Administered via the Hepatic Artery to Rats Bearing Walker 256 Carcinosarcoma in the Liver," J. Pharmacol. Exp. Ther. Dec.;271(3):1267-1273 (1994).

Yanai et al., "Antitumor Effect of Arterial Administration of a Medium-Chain Triglyceride Solutionof an Angiogenesis Inhibitor, TNP-470, in Rabbits Bearing VX-2 Carcinoma," Pharm Res., May;12(5):653-657 (1995).

Zhang et al., "Angiogenesis Inhibitors Specific for Methionine Aminopeptidase 2 as Drugs for Malaria and Leishmaniasis," J. Biomed. Sci., 9(1):34-40 (Jan.-Feb. 2002).

METHODS OF TREATING ISCHEMIC ORGAN DAMAGE AND OTHER DISORDERS

CROSS REFERENCE TO RELATED APPLICATIONS

This application is a continuation of U.S. patent application Ser. No. 15/423,863, now U.S. Pat. No. 9,849,106, filed Feb. 3, 2017, which is a continuation of U.S. patent application Ser. No. 14/776,103, now U.S. Pat. No. 9,597,309, filed Sep. 14, 2015, which is a national stage filing under 35 U.S.C. § 371 of PCT/US2014/028022, filed Mar. 14, 2014, which claims the benefit of U.S. Provisional Application No. 61/787,769, filed on Mar. 15, 2013 and U.S. Provisional Application No. 61/781,926, filed on Mar. 14, 2013; each of these prior applications is incorporated herein by reference in its entirety.

BACKGROUND

Recently, it has been noted that the formation of advanced glycation end products (AGE) and their receptor (RAGE) play an important role in activation of pro-inflammatory states and are involved in numerous pathologic situations.

AGEs result from non-enzymatic glycation and glycoxidation of proteins and lipids. The increased formation and accumulation of AGEs has been reported in such pathophysiological areas such as diabetes, renal failure, aging and inflammation, as well as Alzheimer's disease. The pool of AGEs in vivo reflects not only their endogenous formation, but also their accumulation from exogenous sources including the consumption of foods rich in AGEs and from smoking. During the past two decades, numerous receptors for AGEs have been identified on multiple cell types: endothelial cells, leucocytes, macrophages, mesothelial cells and neuronal cells. The most characterized AGE receptor to-date is RAGE, which is a member of the immunoglobulin super family.

It has been demonstrated that administration of recombinantly produced extracellular domain of RAGE [soluble RAGE (sRAGE)] can block AGE/RAGE interaction, and can lead, for example, to early intense inflammatory response to the excision wound, which promotes better granulation tissue and thus causes early blunting of inflammatory response. Such response can result overall for example, to better wound healing. Further, sRAGE, acting in principle as a decoy receptor, can reduce ischemic organ damage following myocardial infarction or ischemic stroke. In human studies, circulating endogenous sRAGE has been identified as a potential biomarker where decreased levels have been seen in vascular disease states affecting vascular health and function, including coronary artery disease (CAD), hypertension, vascular dementia, atherothrombotic stroke, nonalcoholic steatohepatitis and the diabetic state (type 1 and type 2 diabetes).

Recent studies have also demonstrated a marked increase in the level of advanced glycation end products (AGEs) in the plasma, skin and amyloid fibrils of hemodialysis (HD) patients, with the implication that therapeutic that increased sRAGE would be therapeutically beneficial. Importantly, sRAGE can be used as a biomarker for such inflammatory, renal and other disorders, where low sRAGE can predict a poor outcome. This can be important for candidates in need of an organ or other transplant, and such patients may be required to have an elevated level of sRAGE to become eligible for e.g., such a transplantation procedure. Further, obese, and to some extent, overweight patients may be at a higher risk of such inflammatory and/or renal diseases, and it may be desirable for such patients to lose weight as well as increase sRAGE. Further, patients with established inflammatory microvascular diseases such as that which occurs in diabetes may be at increased risk of poor tissue repair including wound healing, and it may be desirable for such patients to increase sRAGE in order to improve microvascular function.

Adiponectin is an adipocyte-derived, 30 kDa protein that circulates in plasma and has been shown to have multiple functions (see, e.g., Idorn, et al., *Transplant Intl.* 2012, 25, 1194). A correlation is believed to exist between low adiponectin plasma levels and risk of kidney failure, likelihood of successful kidney transplant, and likelihood of getting kidney stones (see, e.g., Idorn, et al., *Transplant Intl.* 2012, 25, 1194; Lin et al., *Diabetes Care* 2007, 30 239; and Fujii et al., *PLOS* 2013, 8, e61343). High molecular weight adiponectin, which is properly folded, is believed to have the highest relative potency on the adiponectin receptor.

Thrombomodulin is a surface glycoprotein that neutralizes thrombin clotting activity and accelerates thrombin-catalyzed activation of protein C (see, e.g., Takano et al., *Blood* 1996, 76, 2024). Thrombomodulin levels are believed to be associated with vascular inflammation and chronic renal disease (see, e.g., Takano et al., *Blood* 1996, 76, 2024; Takahashi et al, *Am. J. Hematol.* 1992, 41, 32; and Califano et al., *Eur. Rev. Med. Pharm. Sci.* 2000, 4, 59).

There is an on-going need for agents that increase sRAGE and/or increase adiponectin levels and/or decrease thrombomodulin levels and can be used to treat indications such as renal disease.

SUMMARY

This disclosure relates in part to methods of modulating certain proteins and markers with MetAP2 inhibitors, such as those disclosed herein. For example, disclosed methods may modulate the levels of one or more of the following: sRAGE, adiponectin (e.g., high molecular weight adiponectin), and thrombomodulin. For example, it has been found that MetAP2 inhibitors, such as those disclosed herein, can increase levels of sRAGE and/or increase levels of adiponectin (e.g., high molecular weight adiponectin) and/or decrease levels of thrombomodulin upon administration to a subject (e.g., an obese subject). Contemplated MetAP-2 inhibitors for use in the disclosed methods include substantially irreversible inhibitors, e.g., a MetAP-2 inhibitor is selected from the group consisting of a fumagillin, fumagillol or fumagillin ketone, siRNA, shRNA, an antibody, or a antisense compound, or O-(4-dimethylaminoethoxycinnamoyl)fumagillol and pharmaceutically acceptable salts thereof. Reversible inhibitors are also contemplated.

Contemplated administration includes oral, subcutaneous administration and/or intravenous administration.

DETAILED DESCRIPTION

Figure 1:
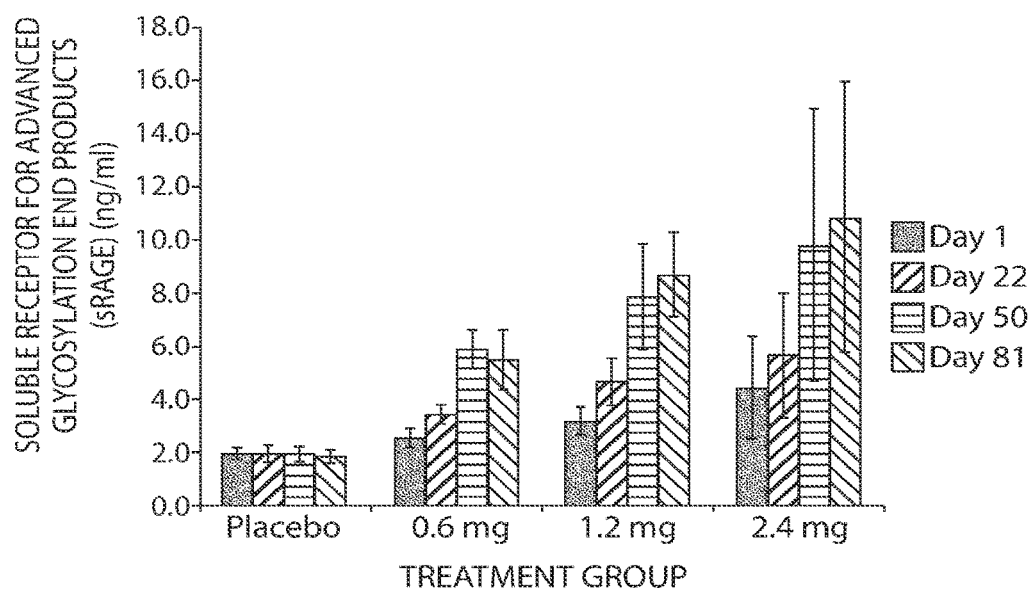
FIG. 1 depicts change in sRAGE plasma levels in patients treated subcutaneously with a disclosed compound.

This disclosure relates in part to methods of modulating certain proteins and markers with MetAP2 inhibitors, such as those disclosed herein. For example, disclosed methods may modulate the levels of one or more of the following: sRAGE, adiponectin (e.g., high molecular weight adiponectin), and thrombomodulin. For example, it has been found that MetAP2 inhibitors, such as those disclosed herein, can increase levels of sRAGE and/or increase levels of adiponectin (e.g., high molecular weight adiponectin) and/or decrease levels of thrombomodulin upon administration to a subject (e.g., an obese subject). Such disclosed compounds therefore may be surprisingly useful in treating patients suffering from diseases associated with one or more of the following: advanced glycation end products, decreased levels of adiponectin (e.g., high molecular weight adiponectin), increased levels of thrombomodulin, and generalized inflammation; such as renal disorders and other indications as described in the disclosed methods.

For example, provided herein is a method for treating or ameliorating a kidney disorder or renal injury (e.g. chronic kidney disease or acute kidney failure) in a patient in need thereof, comprising administering an effective amount of MetAP2 inhibitor. A method of treating, reducing, or ameliorating a renal injury is also provided, for example, an injury selected from the group consisting of an ischemic renal injury and an ischemic-reperfusion renal injury to a kidney, comprising administering an effective amount of MetAP2 inhibitor. As another example, provided herein is a method for preventing, treating, reducing, or ameliorating kidney stones in a patient in need thereof, comprising administering an effective amount of MetAP2 inhibitor.

In an embodiment, a method of improving the transplantation, replacement or surgical outcome of transplanting, replacing or repairing tissue, cells or one or more organs (e.g. a kidney, heart valve (e.g., aortic heart valve replacement or repair) or joints (e.g. knee or hip replacement) is provided in a potential transplant or replacement patient, comprising administering to said patient an effective amount of a MetAP2 inhibitor is provided.

A method of treating a patient suffering from chronic inflammatory disease or impaired wound healing, comprising administering to the patient an effective amount of MetAP2 inhibitor is also contemplated herein.

Methods

Disclosed herein are methods for treating disorders in patients in need of one or more of the following: increased levels of sRAGE, increased levels of adiponectin (e.g., high molecular weight adiponectin), and decreased levels of thrombomodulin. For example, provided herein is a method for treating, or ameliorating a kidney disorder or renal injury in a patient in need thereof, comprising administering an effective amount of MetAP2 inhibitor, such as disclosed herein. Contemplated kidney disorders include chronic kidney disease or acute kidney failure. As another example, provided herein is a method for preventing, treating, reducing, or ameliorating kidney stones in a patient in need thereof, comprising administering to the patient an effective amount of MetAP2 inhibitor, such as disclosed herein.

In some embodiments, a method is provided for treating a patient requiring kidney dialysis, and wherein for example, the patient is in need of fewer or no dialysis treatments or reliance. For example, a patient in need of surgery (e.g. to receive a transplanted organ, cell or tissue) may need to have increased kidney function so such surgery has fewer risks. Such methods comprise administering an effective amount of MetAP2 inhibitor, such as disclosed herein. Methods of treating, reducing, or ameliorating a renal injury selected from the group consisting of an ischemic renal injury and an ischemic-reperfusion renal injury to a kidney, comprising administering an effective amount of MetAP2 inhibitor (such as disclosed herein) are also contemplated).

For example, provided herein is a method of improving the transplantation outcome of transplanting tissue, cells or one or more organs in a potential transplant patient (e.g. a patient that is a potential recipient of a tissue, cell(s) or organ(s) transplant, that is, a patient in need of such transplant), comprising administering to said patient an effective amount of a MetAP2 inhibitor. In other embodiments, such a transplant patient is the potential donor of the tissue, cells (e.g., bone marrow) or organ (e.g., kidney, heart and/or lung). Such patients may also require weight loss before transplantation. Contemplated methods may include improving transplantation outcome in a patient in need of a transplant, and also in need of weight loss before or after such transplant. In an embodiment, a method of treating inflammation and/or rejection associated with transplantation of at least one of a tissue or a plurality of cells into a patient receiving said transplantation, comprising administering to the patient an effective amount of MetAP2 inhibitor.

Also provided herein is a method of improving surgical outcome in a patient in need of cardiac or other surgery (e.g. joint replacement surgery, aortic valve surgery/replacement, organ transplant such as heart, lung, and/or kidney transplant) comprising administering to the patient an effective amount of MetAP2 inhibitor, for example a disclosed MetAP2 inhibitor. For example, such administration may lower or ameliorate the intensity or risk of acute lung injury in such patients and/or reduction in adverse responses to perisurgical ischemic events. For example, provided herein is a method of preparing a patient in need of surgery, wherein the patient is not eligible for said surgery due to increased BMI and/or low sRAGE plasma levels, comprising administering to said patient an effective amount of a MetAP2 inhibitor, thereby improving the outcome of the surgery (e.g., aortic valve surgery, organ replacement surgery, and/or joint replacement surgery)

Also provided herein are methods of treating a disease such as amyloidosis, Alzheimer's disease, kidney failure, or inflammation associated with autoimmunity, arthritis or a wound, inflammatory bowel disease, rheumatoid arthritis, psoriasis, multiple sclerosis, hypoxia, sepsis, organ transplantation, or impaired wound healing in a patient in need thereof, comprising administering to the patient an effective amount of a MetAP2 inhibitor, such as an inhibitor disclosed herein. In an embodiment, provided herein is a method of treating inflammation and/or rejection associated with transplantation of at least one of a tissue or a plurality of cells into a patient receiving said transplantation is also provided herein, wherein the method includes administering to the patient an effective amount of MetAP2 inhibitor.

For example, provided herein is a method of treating a patient suffering from chronic inflammatory disease or impaired wound healing, comprising administering to the patient an effective amount of MetAP2 inhibitor, such as those disclosed herein. Contemplated methods for treating inflammatory disease include inflammatory disease associated with autoimmunity, and/or inflammatory bowel disease, Kawasaki disease, Sjogren's syndrome, systemic lupus erythematosus, rheumatoid arthritis, psoriatic arthritis, chronic obstructive pulmonary disease, juvenile idiopathic arthritis, and psoriasis. In an embodiment, provided herein are methods of treating atherosclerosis, thrombotic stroke, peripheral vascular disease and claudication, peripheral ischemia, and/or right ventricular failure in a patient in need thereof, which include administering to the patient an effective amount of a MetAP2 inhibitor.

Also provided herein are methods of treating diseases associated with diabetic microvascular disease, including retinopathy, nephropathy, neuropathy (microvascular), ischemic heart disease, and peripheral vascular disease in a patient in need thereof, comprising administering to the patient an effective amount of MetAP2 inhibitor, such as those disclosed herein. In an embodiment, provided herein is a method of treating microvascular disease and/or reducing the occurrence or progression of established microvascular disease in a patient in need of treatment or prevention of disease occurrence or progression, comprising administering to the patient an effective amount of MetAP2 inhibitor, such as those disclosed herein.

Also provided herein is a method of treating a neurodegenerative disease in a patient need thereof, comprising administering to the patient an effective amount of a MetAP2 inhibitor. For example, provided herein are methods of treating Alzheimer's disease or amyloidosis, and/or for example dementia, senile dementia, mild cognitive impairment, Alzheimer-related dementia in a patient in need thereof, which include administering to the patient an effective amount of a MetAP2 inhibitor.

Also contemplated here are methods of treating diseases such as amytropic lateral sclerosis, brachial plexus injury, multiple sclerosis, stroke, Huntington's chorea, tardive dyskinesia, hyperkinesias, manias, Morbus Parkinson, steel-Richard syndrome, Down's syndrome, myasthenia gravis, nerve trauma, vascular amyloidosis, cerebral hemorrhage I with amyloidosis, brain inflammation, Friedrich's ataxia, acute confusion disorder, amyotrophic lateral sclerosis, glaucoma, diabetic nephropathy, diabetic retinopathy, nephropathy, vascular complications; atherosclerotic complications, and pulmonary fibrosis in a patient in need thereof, comprising administering to the patient an effective amount of MetAP2 inhibitor, such as those disclosed herein.

For example, contemplated herein are methods of treating diabetic neuropathy in a patient in need thereof, comprising administering to the patient an effective amount of a MetAP2 inhibitor, such as disclosed herein. Contemplated methods of treating include treating third nerve palsy, mononeuropathy or mononeuropathy multiplex, diabetic amyotropy, painful polyneuropathy, autonomic neuropathy, and thoracoabdominal neuropathy in a patient in need thereof, which include administering to the patient an effective amount of a MetAP2 inhibitor.

In some embodiments, a patient being treated for the indications herein is obese, diabetic (e.g. suffering from type 1 or type 2 diabetes), and/or has a glucose metabolism disorder. Contemplated patients may be a human, (e.g. an adult, or a child under 18 years old), or a companion animal such as a cat or a dog.

In an embodiment, the methods provided herein may comprise administering to the patient, on a daily or less than daily basis, a dose of a formulation comprising a therapeutically effective amount of a compound 6-O-(4-dimethylaminoethoxy)cinnamoyl fumagillol or pharmaceutically acceptable salts thereof. Such methods may include administering to the patient a single dose of the formulation about every other day (e.g., every two days); one or two times a week; one, two or three times a week; two or three times a week; twice weekly (e.g. every 3 days, every 4 days, every 5 days, every 6 days or e.g. administered with an interval of about 2 to about 3 days between doses); every three to four days; once a week; every other week; twice monthly; once a month or even less often. It may be appreciated that methods that include administering a single dose on a less frequent basis, may, in some embodiments, be a method directed to amelioriating a condition. Alternatively, a dose of a formulation comprising a therapeutically effective amount of a compound 6-O-(4-dimethylaminoethoxy)cinnamoyl fumagillol or pharmaceutically acceptable salts thereof, may be administered for a first period of time, withheld for a second period of time, and again optionally administered for a third period of time, e.g., alternate dosing regimens. For example, for the first period of time a patient may be administered a disclosed formulation daily, every other day, every three, four or five days, biweekly, monthly, or yearly; during the second period of time (e.g. 1 day, 1 week, 2 weeks, 1 month) no dose is administered; and during e.g. a third period of time, the patient may be administered on a regimen similar or different to the first period of time, for example, every other day, every three, four or five days, biweekly, monthly, or yearly. At each administration or period time, the route of administration may be different or the same as another period of time.

Disclosed methods may include e.g., administering a dose of a disclosed compound on a less than daily basis until a desired sRAGE plasma level and/or a desired adiponectin level and/or a desired thrombomodulin level and/or weight is (are) achieved. In some embodiments, a disclosed method, after the administration of the MetAP2 inhibitor to a patient, may result in a significantly higher plasma level of sRAGE, as compared to before such administration, e.g. may result in a sRAGE plasma level of about 4.0 µg/ml or more, or 12.0 µg/ml or higher, e.g. increased the sRAGE plasma level 2-fold, 3-fold, or even 5-fold or more. In other embodiments, a disclosed method, after the administration of a MetAP2 inhibitor to a patient, may result in significantly higher plasma level of adiponectin as compared to before such administration, e.g. may result in a adiponectin plasma level of about 5.0 µg/ml or more, 6.0 µg/ml or more, 7.0 µg/ml or more, 8.0 µg/ml or more, 10.0 µg/ml or more, or 12.0 µg/ml or higher, e.g. may increase adiponectin plasma levels 2-fold, 3-fold, or even 5-fold or more. In still other embodiments, a disclosed method, after the administration of a MetAP2 inhibitor to the patient, may result in significantly lower plasma level of thrombomodulin, as compared to before such administration, e.g. may result in a thrombomodulin plasma level of less than 4.0 µg/ml, less than 3.0 µg/ml, or less than 2.0 µg/ml.

The therapeutically effective amount administered in the disclosed methods such as those above may also provide a patient with a body weight loss of about 0.3% to about 2%, about 0.4% to about 2%, or about 0.5% to about 2% or more, or about 0.5 kg to about 2 kg or more of the initial patient weight even after an initial dose, or after administration of two doses, or after administering after an first period of time, e.g., such methods may incur weight loss for three or four days or more after administration (e.g. parenteral (for example intravenous) administration) of a single dose. For example, a patient, after receiving a first dose and/or after receiving a subsequent dose, may continue to lose weight for three or four days or more without further administration of a disclosed compound. In some embodiments, administration of an initial first dose, or administration of a first and second dose (e.g., both administered in the same week), may provide about 0.3 kg to about 2 kg or more (e.g., about 0.5 kg to about 2 kg or more) of weight loss. Subsequent administration may result in further weight loss, until a target patient weight is achieved.

In another embodiment, provided herein are effective dosages, e.g. a daily dosage of a MetAP2 inhibitor, that may not substantially modulate or suppress angiogenesis. For example, provided here are methods that include administering doses of MetAP2 inhibitors that are effective for disclosed methods of treatment, but are significantly smaller doses than that necessary to modulate and/or suppress angiogenesis (which may typically require about 12.5 mg/kg to about 50 mg/kg or more). For example, contemplated dosage of a MetAP2 inhibitor in the methods described herein may include administering about 25 mg/day, about 10 mg/day, about 5 mg/day, about 3 mg/day, about 2 mg/day, about 1 mg/day, about 0.75 mg/day, about 0.5 mg/day, about 0.1 mg/day, about 0.05 mg/day, or about 0.01 mg/day.

For example, an effective amount of the drug for disclosed methods in a patient may be about 0.0001 mg/kg to about 25 mg/kg of body weight per day. For example, a contemplated dosage may from about 0.001 to 10 mg/kg of body weight (e.g. per day or every other day), about 0.001 mg/kg to 1 mg/kg of body weight, about 0.001 mg/kg to 0.1 mg/kg of body weight or about 0.005 to about 0.04 mg/kg or about 0.005 to about 0.049 mg/kg of body weight, about 0.01 to about 0.03 mg/kg of body weight, or about 0.005 to about 0.02 mg/kg. In an embodiment a MetAP2 inhibitor such as disclosed herein (e.g. O-(4-dimethlyaminoethoxycinnamoyl)fumagillol), may be administered about 0.005 to about 0.04 mg/kg of a patient, or another dosage amount as disclosed herein (e.g., 0.001 mg/kg). In some embodiments, any of the dosages disclosed herein, including those delineated above, can be provided on a less than daily basis as described herein (e.g., one, two or three times per week or one or two times a week).

Contemplated doses, administered on a less than daily basis, may be a fixed dose, for example, about 0.3 mg, 0.5 mg, 0.6 mg, 1 mg, 2 mg, 1.5 mg, 1.2 mg, 1.8 mg, 1.8 mg, 2.4 mg, 2.5 mg, 3.0 mg, 4 mg, 5 mg or even 6 mg, e.g. about 0.5 mg to about 3.0 mg or about 0.1 mg to about 2 mg. In other embodiments, a therapeutically effective amount is based on excess body weight (or excess adipose tissue), for example, at least about 20 µg of a disclosed compound per kg of excess adipose tissue, (or excess body weight) of the patient, at least about 30 µg of a disclosed compound per kg of excess adipose tissue, (or excess body weight) of the patient, or least about 40 µg per kg or more of excess adipose tissue, (or excess body weight) of the patient, e.g., about 20 µg per kg of excess adipose tissue (or excess body weight) to about 80 µg per kg, about 20 µg per kg of excess adipose tissue (or excess body weight) to about 65 µg per kg, about 40 µg per kg of excess adipose tissue (or excess body weight) to about 80 µg per kg, about 30 µg per kg of excess adipose tissue (or excess body weight) to about 90 µg per kg, about 30 µg per kg of excess adipose tissue (or excess body weight) to about 60 µg per kg, about 40 µg per kg to about 60 µg per kg, or about 35 µg per kg to about 45 µg per kg, or about 35 µg per kg to about 50 µg per kg of excess adipose tissue (or excess body weight). In some embodiments, any of the dosages disclosed herein, including those delineated above, can be provided on a less than daily basis as described herein (e.g., one, two or three times per week or one or two times a week).

For example, provided herein is a method of treating disclosed methods in a patient in need thereof, comprising administering, parenterally (e.g. intravenously or subcutaneously) or non-parenterally (orally), about 0.005 to about 0.04 mg/kg or about 0.01 to about 0.03 mg/kg, or about 0.01 to about 0.1 mg/kg of a MetAP2 inhibitor selected from O-(4-dimethylaminoethoxycinnamoyl)fumagillol and pharmaceutically acceptable salts thereof (for example, an oxalate salt), to said patient. Such a method, upon administration of said MetAP2 inhibitor e.g. daily or weekly, for about 3, 4, 5 or 6 months or more may result in at least a 10%, 20%, 30%, or 40% or more weight loss based on the patient's original weight.

Therapeutically effective doses may be calculated, for example, on the basis of body surface area (BSA), which can be determined using formulae such as those described by Mosteller (Mosteller R D, *N Engl J Med* 1987 Oct. 22; 317(17):1098), in which BSA is calculated in SI units as BSA (m$^2$)=([Height (cm)×Weight (kg)]/3600)$^{1/2}$ (e.g. BSA=SQRT((cm*kg)/3600)), or US units, in which BSA (m$^2$)=([Height (in)×Weight (lbs)]/3131)$^{1/2}$. In some embodiments, the therapeutically effective amount administered (e.g., intravenously) to patient using a disclosed method is about 0.5 mg/m$^2$ to about 3.0 mg/m$^2$, about 0.75 mg/m$^2$ to about 3.0 mg/m$^2$, about 0.5 mg/m$^2$ to about 1.5 mg/m$^2$, about 1.25 mg/m$^2$, or about 0.9 mg/m$^2$ (or approximately 10 to 20 µg per kilo of total body weight) or more of a disclosed compound. In other embodiments, a therapeutically effective amount is based on excess body weight (or excess adipose tissue), for example, at least about 20 µg of a disclosed compound per kg of excess adipose tissue, (or excess body weight) of the patient, at least about 30 µg of a disclosed compound per kg of excess adipose tissue, (or excess body weight) of the patient, or least about 40 µg per kg or more of excess adipose tissue, (or excess body weight) of the patient, e.g., about 20 µg per kg of excess adipose tissue (or excess body weight) to about 80 µg per kg, about 20 µg per kg of excess adipose tissue (or excess body weight) to about 65 µg per kg, about 40 µg per kg of excess adipose tissue (or excess body weight) to about 80 µg per kg, about 30 µg per kg of excess adipose tissue (or excess body weight) to about 90 µg per kg, about 30 µg per kg of excess adipose tissue (or excess body weight) to about 60 µg per kg, about 40 µg per kg to about 60 µg per kg, or about 35 µg per kg to about 45 µg per kg, or about 35 µg per kg to about 50 µg per kg of excess adipose tissue (or excess body weight). In some embodiments, any of the dosages disclosed herein, including those delineated above, can be provided on a less than daily basis as described herein (e.g., one, two or three times per week or one or two times a week).

Disclosed or contemplated treatment regimens can include a corrective phase, during which a MetAP2 inhibitor dose sufficient to provide an increase in levels of sRAGE, e.g., in order to treat or correct a disclosed disorder, followed by a maintenance phase, during which a lower or equivalent MetAP2 inhibitor dose sufficient to prevent re-development of a disclosed disorder may be administered.

Obesity and being overweight refer to an excess of fat in proportion to lean body mass. Excess fat accumulation is associated with increase in size (hypertrophy) as well as number (hyperplasia) of adipose tissue cells. Obesity is variously measured in terms of absolute weight, weight: height ratio, degree of excess body fat, distribution of subcutaneous and/or visceral fat, and societal and esthetic norms. A common measure of body fat is Body Mass Index (BMI). The BMI refers to the ratio of body weight (expressed in kilograms) to the square of height (expressed in meters). Body mass index may be accurately calculated using the formulas: SI units: BMI=weight (kg)/(height$^2$ (m$^2$), or US units: BMI=(weight (lb)*703)/(height$^2$ (in$^2$).

In accordance with the U.S. Centers for Disease Control and Prevention (CDC), an overweight adult has a BMI of 25 kg/m$^2$ to 29.9 kg/m$^2$, and an obese adult has a BMI of 30 kg/m$^2$ or greater. A BMI of 40 kg/m$^2$ or greater is indicative of morbid obesity or extreme obesity. For children, the definitions of overweight and obese take into account age, stature, and gender as they relate to what are appropriate amounts of body fat and do not strictly rely on upon BMI calculations. It may be appreciated that for certain patients (e.g., certain ethnic groups, e.g. Asian), a lower BMI may be consideration overweight or obese. In some embodiments, a patient has a BMI of 25 kg/m$^2$ to 29.9 kg/m$^2$; a BMI of 30 kg/m$^2$ or greater; or a BMI of 27 kg/m$^2$ and is suffering from weight related comorbidity.

BMI does not account for the fact that excess adipose can occur selectively in different parts of the body, and development of adipose tissue can be more dangerous to health in some parts of the body rather than in other parts of the body. For example, "central obesity", typically associated with an "apple-shaped" body, results from excess adiposity especially in the abdominal region, including belly fat and intra-abdominal or visceral fat, and carries higher risk of co-morbidity than "peripheral obesity", which is typically associated with a "pear-shaped" body resulting from excess adiposity especially on the hips. Measurement of waist/hip circumference ratio (WHR) can be used as an indicator of central obesity. A minimum WHR indicative of central obesity has been variously set, and a centrally obese adult typically has a WHR of about 0.85 or greater if female and about 0.9 or greater if male. Methods of determining whether a subject is overweight or obese that account for the ratio of excess adipose tissue to lean body mass may involve obtaining a body composition of the subject. Body composition can be obtained by measuring the thickness of subcutaneous fat in multiple places on the body, such as the abdominal area, the subscapular region, arms, buttocks and thighs. These measurements are then used to estimate total body fat with a margin of error of approximately four percentage points. Another method is bioelectrical impedance analysis (BIA), which uses the resistance of electrical flow through the body to estimate body fat. Another method is using a large tank of water to measure body buoyancy. Increased body fat will result in greater buoyancy, while greater muscle mass will result in a tendency to sink. Yet another method is fan-beam dual energy X-ray absorptiometry (DEXA). DEXA allows body composition, particularly total body fat and/or regional fat mass, to be determined non-invasively.

Excess body weight may be assessed, for example, by comparing the weight of a patient in need of treatment to the weight of the same patient that would achieve a desired, e.g. non-obese, BMI (e.g. a desired BMI of about 25 or less). For example, excess body weight of a 1.6 m in height patient weighing 89.6 kg (and having a BMI of 35) may be found by calculating the weight required for a BMI of 25 (i.e., about 64 kg); the initial excess body weight of such patient would about 89.6−64=25.6 kg.

MetAP2 Inhibitors

MetAP2 inhibitors refer to a class of molecules that inhibit or modulate the activity of MetAP2, e.g., the ability of MetAP2 to cleave the N-terminal methionine residue of newly synthesized proteins to produce the active form of the protein, or the ability of MetAP2 to regulate protein synthesis by protecting the subunit of eukaryotic initiation factor-2 (eIF2) from phosphorylation, or the ability of MetAP2 to attenuate activity of extracellular regulated kinase (ERK) activity by protecting the kinase or its modulators from phosphorylation.

Exemplary MetAP2 inhibitors may include irreversible inhibitors that covalently bind to MetAP2. For example, such irreversible inhibitors include fumagillin, fumagillol, and fumagillin ketone.

Derivatives and analogs of fumagillin, and pharmaceutically acceptable salts thereof are contemplated herein as irreversible MetAP2 inhibitors, such as O-(4-dimethylaminoethoxycinnamoyl)fumagillol (also referred to herein as Compound A), O-(3,4,5-trimethoxycinnamoyl)fumagillol, O-(4-chlorocinnamoyl)fumagillol; O-(4-aminocinnamoyl) fumagillol; O-(4-dimethylaminoethoxycinnamoyl)fumagillol; O-(4-methoxycinnamoyl)fumagillol; O-(4-dimethylaminocinnamoyl)fumagillol; O-(4-hydroxycinnamoyl) fumagillol; O-(3,4-dimethoxycinnamoyl)fumagillol; O-(3,4-methylenedioxycinnamoyl)fumagillol; O-(3,4,5-trimethoxycinnamoyl)fumagillol; O-(4-nitrocinnamoyl) fumagillol; O-(3,4-dimethoxy-6-aminocinnamoyl) fumagillol; O-(4-acetoxy-3,5-dimethoxycinnamoyl) fumagillol; O-(4-ethylaminocinnamoyl)fumagillol; O-(4-ethylaminoethoxycinnamoyl)fumagillol; O-(3-dimethylaminomethyl-4-methoxycinnamoyefumagillol; O-(4-trifluoromethylcinnamoyl)fumagillol; O-(3,4-dimethoxy-6-nitrocinnamoyl)fumagillol; O-(4-acetoxycinnamoyl)fumagillol; O-(4-cyanocinnamoyl)fumagillol; 4-(4-methoxycinnamoyl)oxy-2-(1,2-epoxy-1,5-dimethyl-4-hexenyl)-3-methoxy-1-chloromethyl-1-cyclohexanol; O-(3,4,5-trimethoxycinnamoyl)fumagillol; O-(4-dimethylaminocinnamoyl)fumagillol; O-(3,4,5-trimethoxycinnamoyl)oxy-2-(1,2-epoxy-1,5-dimethyl-4-hexenyl)-3-m-ethoxy-1-chloromethyl-1-cyclohexanol; O-(4-dimethylaminocinnamoyl)oxy-2-(1,2-epoxy-1,5-dimethyl-4-hexenyl)-3-me-thoxy-1-chloromethyl-1-cyclohexanol; O-(3,5-dimethoxy-4-hydroxycinnamoyl)fumagillol or O-(chloracetyl-carbamoyl) fumagillol (TNP-470), and/or pharmaceutically acceptable salts thereof (e.g. O-(4-dimethylaminoethoxycinnamoyl)fumagillol oxalate, e.g., hemi-oxalate salt of compound A).

Certain solid forms of fumagillin derivatives and analogs, and pharmaceutically acceptable salts thereof, are contemplated herein as MetAP2 inhibitors, e.g., a crystalline form of compound A, free base, characterized by a powder X-ray diffraction pattern having characteristic peaks in degrees 2θ at about 13.3, 17.4, and 19.9 (e.g., characterized by a powder X-ray diffraction pattern having characteristic peaks in degrees 2θ at 7.1, 13.3, 16.3, 17.4, 18.6, 19.4, and 19.9, or for example, characterized by a powder X-ray diffraction pattern having characteristic peaks in degrees 2θ at 5.2, 7.1, 10.4, 13.3, 14.2, 16.3, 17.4, 18.6, 19.4, and 19.9, obtained using Cu Kα radiation), which is described in, e.g., U.S. Pat. No. 8,349,891, which is incorporated herein by reference in its entirety.

Fumagillin, and some derivatives thereof, have a carboxylic acid moiety and can be administered in the form of the free acid. Alternatively, contemplated herein are pharmaceutically acceptable salts of fumagillin, fumagillol, and derivatives thereof.

Pharmaceutically acceptable salts illustratively include those that can be made using the following bases: ammonia, L-arginine, benethamine, benzathene, betaine, bismuth, calcium hydroxide, choline, deanol, diethanolamine, diethylamine, 2-(diethylamino)ethanol, ethylenediamine, N-methylglucarnine, hydrabamine, 1H-imidazole, lysine, magnesium hydroxide, 4-(2-hydroxyethyl)morpholine, piperazine, potassium hydroxide, 1-(2-hydroxyethyl)pyrrolidine, sodium hydroxide, triethanolamine, zinc hydroxide, diclyclohexlamine, or any other electron pair donor (as described in Handbook of Pharmaceutical Salts, Stan & Wermuth, VHCA and Wiley, Uchsenfurt-Hohestadt Germany, 2002). Contemplated pharmaceutically acceptable salts may include hydrochloric acid, bromic acid, sulfuric acid, phosphoric acid, nitric acid, formic acid, acetic acid, trifluoroacetic acid, oxalic acid, fumaric acid, tartaric acid, maleic acid, methanesulfonic acid, benzenesulfonic acid or para-toluenesulfonic acid.

Esters of the present invention may be prepared by reacting e.g. fumagillin or fumagillol with the appropriate acid under standard esterification conditions described in the literature (Houben-Weyl 4th Ed. 1952, Methods of Organic Synthesis). Suitable fumagillin esters include ethyl methanoate, ethyl ethanoate, ethyl propanoate, propyl methanoate, propyl ethanoate, and methyl butanoate.

In another embodiment, contemplated irreversible inhibitors of MetAP2 may include a siRNA, shRNA, an antibody or an antisense compound of MetAP2.

Further examples of reversible and irreversible MetAP2 inhibitors are provided in the following references, each of which is hereby incorporated by reference: Olson et al. (U.S. Pat. No. 7,084,108 and WO 2002/042295), Olson et al. (U.S. Pat. No. 6,548,477; U.S. Pat. No. 7,037,890; U.S. Pat. No. 7,084,108; U.S. Pat. No. 7,268,111; and WO 2002/042295), Olson et al. (WO 2005/066197), Hong et al. (U.S. Pat. No. 6,040,337)., Hong et al. (U.S. Pat. No. 6,063,812 and WO 1999/059986), Lee et al. (WO 2006/080591), Kishimoto et al. (U.S. Pat. No. 5,166,172; U.S. Pat. No. 5,698,586; U.S. Pat. Nos. 5,164,410; and 5,180,738), Kishimoto et al. (U.S. Pat. No. 5,180,735), Kishimoto et al. (U.S. Pat. No. 5,288,722), Kishimoto et al. (U.S. Pat. No. 5,204,345), Kishimoto et al. (U.S. Pat. No. 5,422,363), Liu et al. (U.S. Pat. No. 6,207,704; U.S. Pat. No. 6,566,541; and WO 1998/056372), Craig et al. (WO 1999/057097), Craig et al. (U.S. Pat. No. 6,242,494), BaMaung et al. (U.S. Pat. No. 7,030,262), Comess et al. (WO 2004/033419), Comess et al. (US 2004/0157836), Comess et al. (US 2004/0167128), Henkin et al. (WO 2002/083065), Craig et al. (U.S. Pat. No. 6,887,863), Craig et al. (US 2002/0002152), Sheppard et al. (2004, Bioorganic & Medicinal Chemistry Letters 14:865-868), Wang et al. (2003, Cancer Research 63:7861-7869), Wang et al. (2007, Bioorganic & Medicinal Chemistry Letters 17:2817-2822), Kawai et al. (2006, Bioorganic & Medicinal Chemistry Letters 16:3574-3577), Henkin et al. (WO 2002/026782), Nan et al. (US 2005/0113420), Luo et al. (2003, J. Med. Chem., 46:2632-2640), Vedantham et al. (2008, J. Comb. Chem., 10:195-203), Wang et al. (2008, J. Med. Chem., 51 (19):6110-20), Ma et al. (2007, BMC Structural Biology, 7:84) and Huang et al. (2007, J. Med. Chem., 50:5735-5742), Evdokimov et al. (2007, PROTEINS: Structure, Function, and Bioinformatics, 66:538-546), Garrabrant et al. (2004, Angiogenesis 7:91-96), Kim et al. (2004, Cancer Research, 64:2984-2987), Towbin et al. (2003, The Journal of Biological Chemistry, 278(52):52964-52971), Marino Jr. (U.S. Pat. No. 7,304,082), Kallender et al. (U.S. patent application number 2004/0192914), and Kallender et al. (U.S. patent application numbers 2003/0220371 and 2005/0004116). Other MetAP2 inhibitors contemplated herein are disclosed in U.S. Pat. No. 8,349,891, U.S. Ser. No. 61/310,776; 61/293,318; 61/366,650, PCT/US10/52050, PCTUS11/055987, PCTUS11/044864, PCTUS12/028068, PCTUS12/022721, PCTUS12/36789, PCTUS12/36792, PCTUS12/36793 (all of the above are hereby incorporated by reference in their entirety).

For example, contemplated MetAP2 inhibitors may include one or more of:

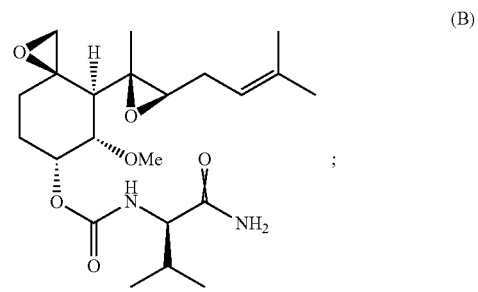

(B)

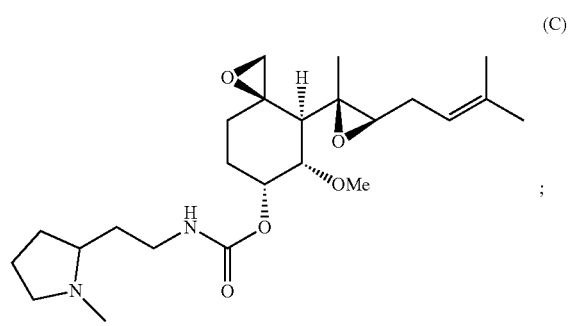

(C)

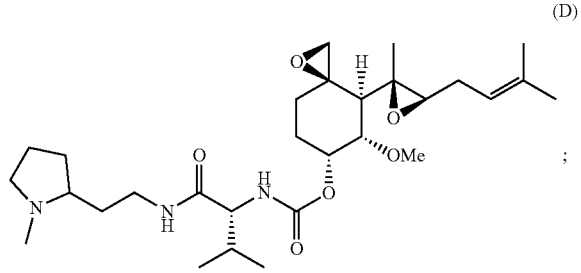

(D)

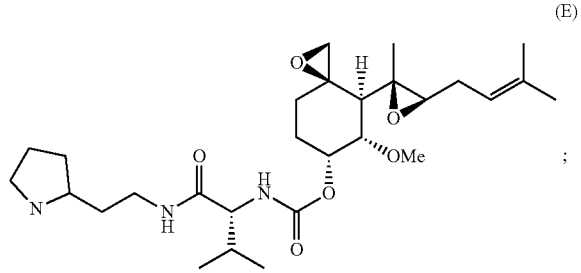

(E)

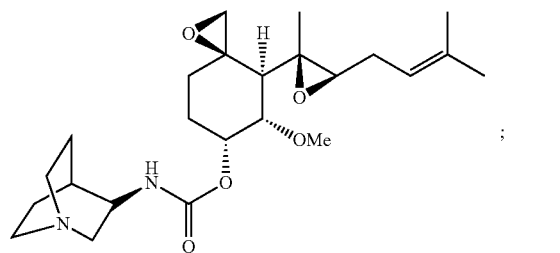

(F)

-continued

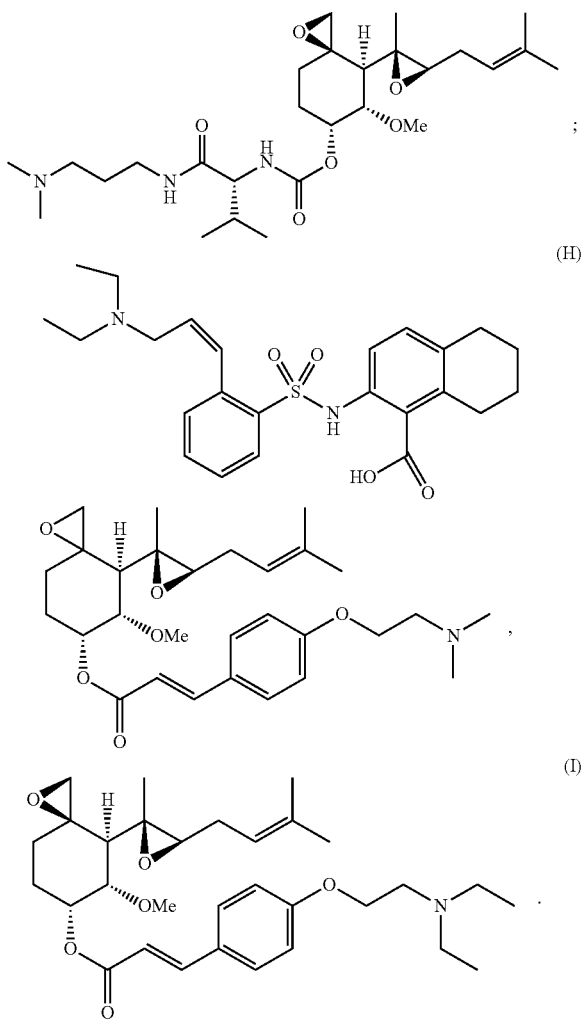

EXAMPLES

The examples which follow are intended in no way to limit the scope of this invention but are provided to illustrate aspects of the disclosed methods. Many other embodiments of this invention will be apparent to one skilled in the art.

Example 1: sRAGE Study

Obese patients were treated in three cohorts with intravenous administration of a formulation of the compound A. The compound was intravenously administered to each patient of a cohort (except for a placebo cohort) twice weekly for 81 days. Each of patients in the three non-placebo cohorts received either 0.6 mg of compound A (cohort 1); 1.2 mg (cohort 2); or 2.4 mg (cohort 3) doses of the compound at the time of administration. The trial was conducted under the appropriate government and medical supervision.

As shown in FIG. 1, administration of 6-O-(4-dimethyl-aminoethoxy)cinnamoyl fumagillol oxalate causes an increase in the in levels of sRAGE in patients' serum.

Figure 2:
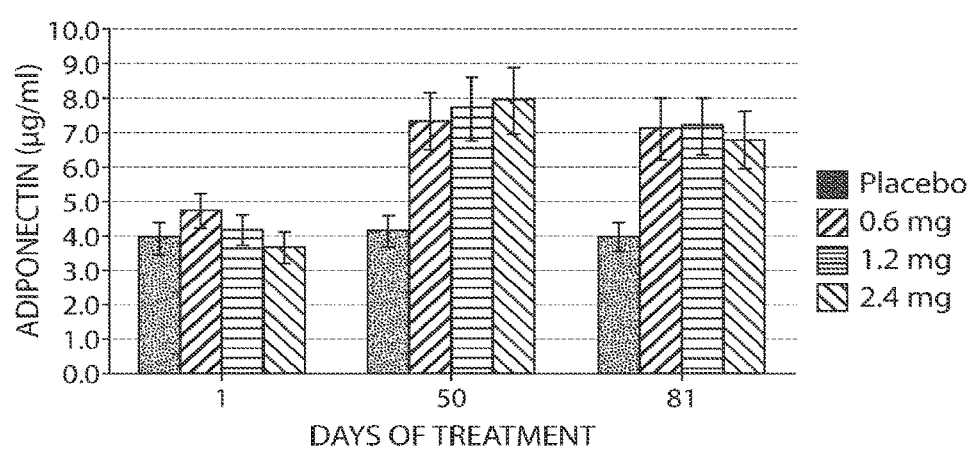
FIG. 2 is a graph showing dose proportional increases in plasma adiponectin after twelve weeks (81 days) of subcutaneous treatment with Compound A at doses of 0, 0.6, 1.2 and 2.4 mg.
Figure 3:
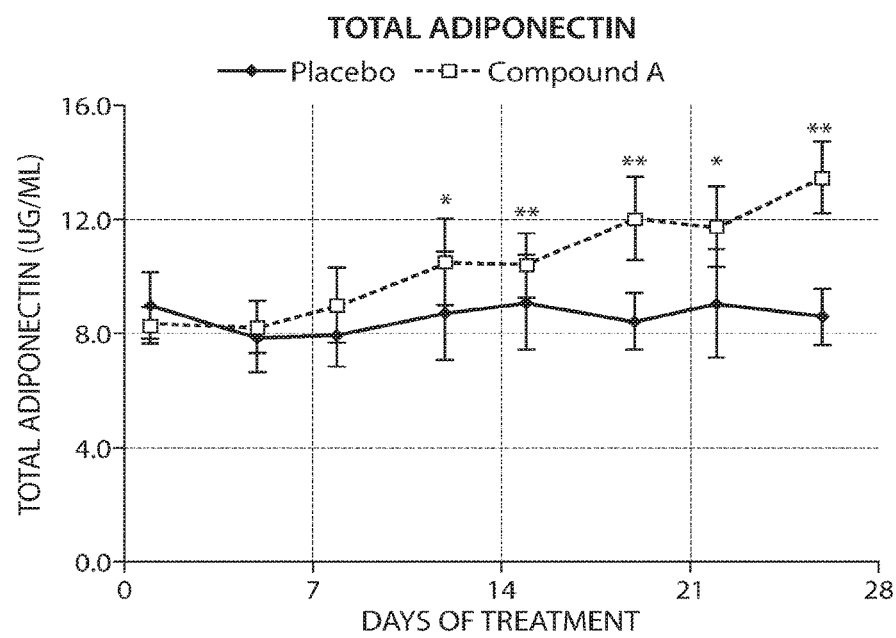
FIG. 3 is a graph showing increases in total plasma adiponectin after 4 weeks of intravenous treatment with Compound A versus placebo (total adiponectin assessed using the ALPCO system (ELISA).
Figure 4:
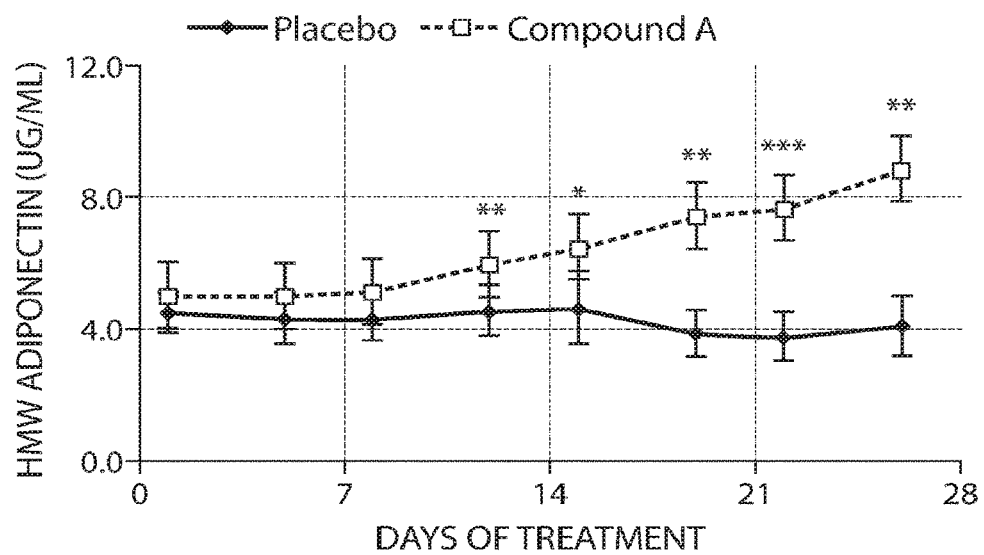
FIG. 4 is a graph showing increases in the high molecular weight form of adiponectin after 4 weeks of intravenous treatment with 1.9 mg of Compound A versus placebo.
Figure 5:
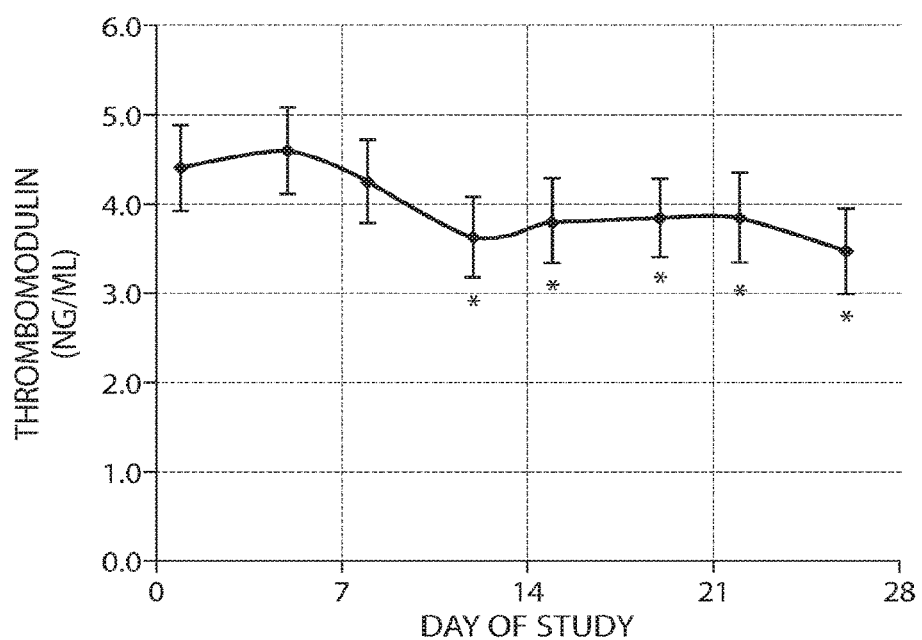
FIG. 5 is a graph showing mean group changes in thrombomodulin concentrations in plasma samples collected prior to intravenous administration of compound A for days 1 (baseline), 5, 8, 15, 19, 22, and 26 for patients treated with 0.9 mg/m$^2$ of Compound A.

FIGS. 2-5 show the effects of compound A on adiponectin and thrombomodulin levels in obese patients treated with intravenous administration of a formulation of the compound A. As shown in FIG. 2, dose proportional increases in plasma adiponectin are observed after twelve weeks (81 days) of treatment with Compound A at doses of 0 (placebo), 0.6, 1.2 and 2.4 mg. As shown in FIG. 3, increases in total plasma adiponectin are observed after 4 weeks of treatment with Compound A versus placebo. As shown in FIG. 4, increases in the high molecular weight form of adiponectin are observed after 4 weeks of treatment with 1.9 mg of Compound A versus placebo. FIG. 5 shows mean group changes in thrombomodulin concentrations in plasma samples collected prior to intravenous administration of compound A for days 1 (baseline), 5, 8, 15, 19, 22, and 26 for patients treated with 0.9 mg/m2 of Compound A.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method of treating ischemic organ damage following myocardial infarction or ischemic stroke in a patient in need thereof, comprising administering to the patient an effective amount of a MetAP2 inhibitor that covalently binds to MetAP2, wherein the MetAP2 inhibitor is an irreversible MetAP2 inhibitor that covalently binds to MetAP2, wherein said effective amount does not substantially modulate or suppress angiogenesis.

2. The method of claim 1, wherein the MetAP2 inhibitor is selected from the group consisting of 6-O-(4-dimethyl-aminoethoxycinnamoyl)fumagillol and pharmaceutically acceptable salts thereof.

3. The method of claim 1, wherein the MetAP2 inhibitor is administered parenterally or non-parenterally.

4. The method of claim 1, wherein after the administration of the MetAP2 inhibitor, the patient has a significantly higher plasma level of sRAGE.

5. The method of claim 1, comprising parenterally administering 2 or 3 times a week a pharmaceutically effective amount of the MetAP2 inhibitor to said patient.

6. The method of claim 5, wherein parenterally administering is subcutaneously administering.

7. The method of claim 1, wherein the ischemic organ damage is ischemic renal injury.

8. A method of treating a patient suffering from ischemic renal injury or ischemic reperfusion renal injury, and in need thereof, comprising administering to the patient an effective amount of a MetAP2 inhibitor, wherein said effective amount does not substantially modulate or suppress angiogenesis.

9. The method of claim 8, wherein after the administration of the MetAP2 inhibitor, the patient has a significantly higher plasma level of sRAGE.

10. The method of claim 9, wherein after the administration of the MetAP2 inhibitor, the patient has a significantly lower plasma level of thrombomodulin.

* * * * *